(12) United States Patent
Von Arx et al.

(10) Patent No.: US 7,519,430 B2
(45) Date of Patent: Apr. 14, 2009

(54) DYNAMIC TELEMETRY ENCODING FOR AN IMPLANTABLE MEDICAL DEVICE

(75) Inventors: Jeffrey A. Von Arx, Minneapolis, MN (US); Prashant Rawat, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 603 days.

(21) Appl. No.: 10/870,324

(22) Filed: Jun. 17, 2004

(65) Prior Publication Data

US 2005/0283208 A1  Dec. 22, 2005

(51) Int. Cl.
*A61N 1/00* (2006.01)

(52) U.S. Cl. ....................................................... 607/60

(58) Field of Classification Search ............... 607/60, 607/85; 128/903; 341/68; 604/65; 369/53.22; 711/118, 119
See application file for complete search history.

(56) References Cited

U.S. PATENT DOCUMENTS

| | | | |
|---|---|---|---|
| 3,914,586 A * | 10/1975 | McIntosh | ...... 341/68 |
| 4,441,498 A | 4/1984 | Nordling | |
| 4,519,401 A | 5/1985 | Ko et al. | |
| 4,543,954 A | 10/1985 | Cook et al. | |
| 4,945,909 A | 8/1990 | Fearnot et al. | |
| 5,171,977 A | 12/1992 | Morrison | |
| 5,230,003 A | 7/1993 | Dent et al. | |
| 5,342,408 A | 8/1994 | deCoriolis et al. | |
| 5,350,412 A | 9/1994 | Hoegnelid et al. | |
| 5,370,666 A | 12/1994 | Lindberg et al. | |
| 5,476,488 A | 12/1995 | Morgan et al. | |
| 5,630,835 A * | 5/1997 | Brownlee | ...... 607/60 |
| 5,683,432 A | 11/1997 | Goedeke et al. | |
| 5,752,977 A | 5/1998 | Grevious et al. | |
| 5,843,139 A | 12/1998 | Goedeke et al. | |
| 5,881,101 A | 3/1999 | Furman et al. | |
| 5,895,485 A * | 4/1999 | Loechel et al. | ...... 711/119 |
| 6,044,485 A | 3/2000 | Dent et al. | |
| 6,093,146 A | 7/2000 | Filangeri | |
| 6,167,310 A | 12/2000 | Grevious | |
| 6,169,925 B1 | 1/2001 | Villaseca et al. | |

(Continued)

FOREIGN PATENT DOCUMENTS

WO    WO-95/00202 A1    1/1995

(Continued)

OTHER PUBLICATIONS

Katoozi, M., et al., "On-Demand Retransmission of Data With an Implantable Medical Device", U.S. Appl. No. 10/870,328, filed Jun. 17, 2004.

(Continued)

*Primary Examiner*—George Manuel
(74) *Attorney, Agent, or Firm*—Schwegman, Lundberg & Woessner, P.A.

(57) ABSTRACT

A telemetry system provides a selectable encoding protocol, including, for example, a plurality of redundancy levels, where the encoding protocol is selected based on a measure of transmission efficiency. For example, later messages are transmitted using an increased redundancy if a prior message exhibits a low signal to noise ratio. A communication session is initiated using a first level of redundancy and the level is adjusted based on a channel characteristic or a measured parameter.

72 Claims, 3 Drawing Sheets

U.S. PATENT DOCUMENTS

| | | | |
|---|---|---|---|
| 6,336,900 B1 | 1/2002 | Alleckson et al. | |
| 6,336,903 B1 | 1/2002 | Bardy | |
| 6,385,318 B1 | 5/2002 | Oishi | |
| 6,424,867 B1 | 7/2002 | Snell et al. | |
| 6,434,429 B1 | 8/2002 | Kraus et al. | |
| 6,443,891 B1 | 9/2002 | Grevious | |
| 6,456,875 B1 | 9/2002 | Wilkinson et al. | |
| 6,470,215 B1 | 10/2002 | Kraus et al. | |
| 6,562,001 B2 * | 5/2003 | Lebel et al. | 604/65 |
| 6,564,104 B2 | 5/2003 | Nelson et al. | |
| 6,564,105 B2 | 5/2003 | Starkweather et al. | |
| 6,574,503 B2 | 6/2003 | Ferek-Petric | |
| 6,574,509 B1 | 6/2003 | Kraus et al. | |
| 6,574,510 B2 | 6/2003 | Von Arx et al. | |
| 6,585,644 B2 | 7/2003 | Lebel et al. | |
| 6,600,952 B1 | 7/2003 | Snell et al. | |
| 6,602,191 B2 | 8/2003 | Quy | |
| 6,622,043 B1 | 9/2003 | Kraus et al. | |
| 6,622,050 B2 | 9/2003 | Thompson | |
| 6,648,821 B2 | 11/2003 | Lebel et al. | |
| 6,687,546 B2 | 2/2004 | Lebel et al. | |
| 7,274,642 B2 * | 9/2007 | Sako et al. | 369/53.22 |
| 2002/0019606 A1 | 2/2002 | Lebel et al. | |
| 2002/0049480 A1 | 4/2002 | Lebel et al. | |
| 2002/0065539 A1 | 5/2002 | Von Arx et al. | |
| 2002/0065540 A1 | 5/2002 | Lebel et al. | |
| 2002/0147388 A1 | 10/2002 | Mass et al. | |
| 2003/0114898 A1 | 6/2003 | Von Arx et al. | |
| 2004/0030260 A1 | 2/2004 | Von Arx | |
| 2004/0102815 A1 | 5/2004 | Balczewski et al. | |
| 2004/0260363 A1 | 12/2004 | Arx et al. | |
| 2005/0283209 A1 | 12/2005 | Katoozi et al. | |
| 2005/0288738 A1 | 12/2005 | Bange et al. | |
| 2006/0025834 A1 * | 2/2006 | Von Arx et al. | 607/60 |

FOREIGN PATENT DOCUMENTS

| | | |
|---|---|---|
| WO | WO-2005/099817 A1 | 10/2005 |

OTHER PUBLICATIONS

Prosecution File History of U.S. Appl. No. 10/870,328, (as of Oct. 19, 2007),36 pgs.

Prosecution File History of U.S. Appl. No. 11/101,142, (as of Oct. 19, 2007),27 pgs.

"Prosecution File History of U.S. Appl. No. 10/269,905, filed Oct. 11, 2002, Prosecution File History", (now US 7,069,086), 32 pgs.

* cited by examiner

DYNAMIC TELEMETRY ENCODING FOR AN IMPLANTABLE MEDICAL DEVICE

CROSS-REFERENCE TO RELATED DOCUMENTS

This document is related to U.S. patent application Ser. No. 10/870,328, entitled "ON DEMAND RETRANSMISSION OF DATA WITH AN IMPLANTABLE MEDICAL DEVICE," filed Jun. 17, 2004 by Katoozi et al., and is incorporated herein by reference.

This document is related to U.S. patent application Ser. No. 10/025,223, entitled "A TELEMETRY DUTY CYCLE MANAGEMENT SYSTEM FOR AN IMPLANTABLE MEDICAL DEVICE," filed Dec. 19, 2001 by Von Arx et al., and is incorporated herein by reference.

TECHNICAL FIELD

This document pertains generally to telemetry for medical devices, and more particularly, but not by way of limitation, to selecting and implementing a message encoding protocol based on a channel characteristic or other parameter.

BACKGROUND

A typical implantable medical device is configured to enable wireless communications with an external device, such as a programmer or a repeater, using inductive telemetry. Inductive telemetry operates using a near field inductive coupling and provides robust communication.

While inductive telemetry tolerates interference from noise sources, many users find that the relatively short communication range is inconvenient.

What is needed is an improved telemetry method and system.

BRIEF DESCRIPTION OF THE DRAWINGS

In the drawings, which are not necessarily drawn to scale, like numerals describe substantially similar components throughout the several views. Like numerals having different letter suffixes correspond to different instances of substantially similar components. The drawings illustrate generally, by way of example, but not by way of limitation, various embodiments of the present subject matter.

DETAILED DESCRIPTION

Figure 1:
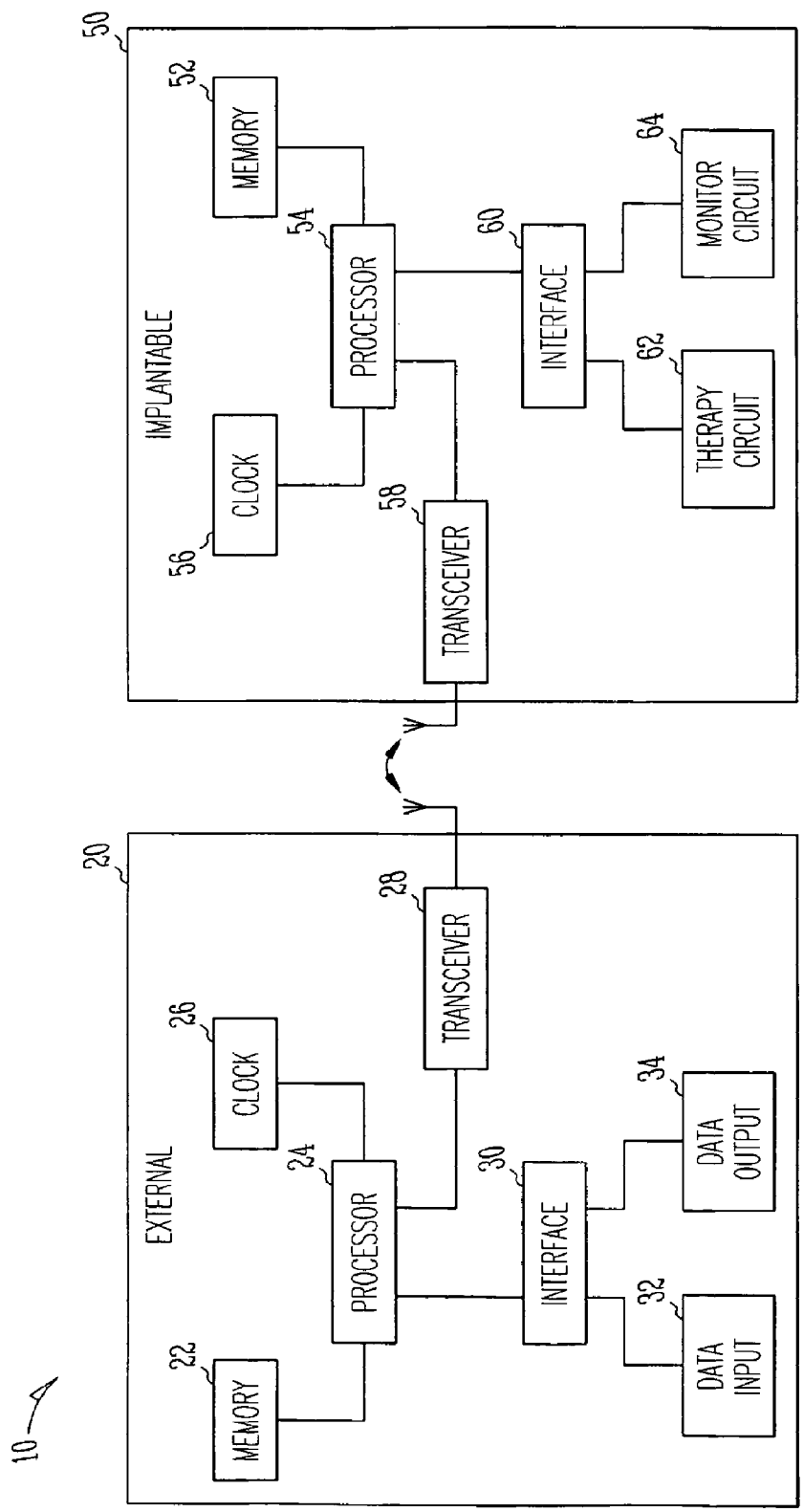
FIG. 1 illustrates an example of a system having an external device and an implantable device configured to communicate wirelessly.

In the following detailed description, reference is made to the accompanying drawings which form a part hereof and which illustrate specific embodiments. The various examples are described in sufficient detail to enable those skilled in the art to practice the subject matter, and it is to be understood that the examples may be combined, or that other examples may be utilized and that structural, logical and electrical changes may be made without departing from the scope of the present subject matter. The detailed description is, therefore, not to be taken in a limiting sense and the scope of the present subject matter is defined by the appended claims and their equivalents.

In this document, the articles "a" and "an" denote both the singular and the plural form of the associated noun, and, unless otherwise noted, the term "or" is used in the non-exclusive sense. Furthermore, all publications, patents, and documents referred to in this document are incorporated by reference herein in their entirety, as though individually incorporated by reference. In the event of inconsistencies between this document and those publications, patents and documents herein incorporated by reference, this document is controlling.

In this document, reference is made to the sending device and the receiving device. Unless otherwise provided, the sending device includes either the external device or the implantable device and accordingly, the receiving device includes either the implantable device or the external device, respectively. In other words, at any given time, the external device may be the sending device and the implantable device may be the receiving device and at a later time, the device roles are reversed.

A unit of digital data is variously referred to as a packet or a frame. It will be understood that such units of data may differ in the content and the length as well as other parameters. Each such unit of data includes a message and the data throughput rate (or throughput) is the rate at which the message is conveyed between the sending device and the receiving device. The data throughput rate will change with a change in the level of redundancy, however the raw data rate will remain substantially constant. The data can include, for example, real time data, such as electrogram data and markers or stored data, such as device identification information.

System Overview

The present subject matter includes methods and systems for transmitting data between an implantable medical device and an external device. The data throughput rate is dynamically adjusted to provide efficient communication over a particular range with an error rate not exceeding a particular rate.

A relationship exists between the data throughput rate, the communication range the error rate and the level of redundancy. At a particular level of redundancy and a given data throughput rate, the effective communication range can be specified based on an acceptable error rate and conversely, for a particular data throughput rate and error rate, the range can be determined. Under certain circumstances, a reduction in the level of redundancy yields an increased error rate and data throughput rate and a reduced range. Conversely, an increase in the level of redundancy yields a decreased error rate and data throughput rate and an increased range.

In one example, the level of redundancy is selected to provide an acceptable error rate, communication range and data throughput rate. In general, the error rate, communication range and data throughput rate are also determined based on selection of an encoding protocol. Accordingly, one example provides that a plurality of encoding protocols are available (from either or both of the implantable device and the external device) and the selection of the encoding protocol is determined based on a channel characteristic or other parameter. Thus, the data throughput rate, range and error rate, are selectable for any particular communication channel and particular encoding protocol (or level of redundancy).

For example, in a clinical setting, an external device (sometimes referred to as a programmer) is used to communicate with the implantable device. A programmer, in various examples, includes a display screen, a printer or other output device that conveys data to an operator and receives data or other instructions entered by a human operator or received from an input interface.

Using the programmer, a relatively high data rate (typically 100 kbps or more) at a moderate communication range of approximately 2-3 meters is generally acceptable. Such a moderate communication range reduces the deleterious effects of interference sources (such as may originate from an adjacent clinic office) which may result in errors.

For remote monitoring in a patient's home, for example, an external device, sometimes referred to as a repeater, is used to communicate with the implantable device. A repeater, in various examples, includes a device having an interface to a communication network that enables remote monitoring or programming. A repeater communicates between the implantable device and the communication network to effectively extend the communication range. In one example, a repeater is connected to a telephone line within a home thus allowing medical personnel to monitor an implantable device of an occupant of the home via the plain old telephone service (POTS) network. In one example, a repeater is communicatively coupled to a network, such as the internet, by means of a wired or wireless interface. In various examples, the repeater is coupled to a cable modem, a dial-up modem or other interface for wired communication using a network.

Using the repeater, a greater wireless communication range is achieved and lower data throughput rates are generally adequate. In one example, the range is approximately 10 meters and the data throughput rate is approximately 10 kbps, however ranges and data throughput rates other than these are also contemplated. The relatively longer range permits the patient to remain ambulatory while providing continuous monitoring over an extended time period.

By selecting an encoding protocol according to the type of communication mode to be conducted, the communication range and data throughput rate is also selectable. Exemplary communication modes include the clinical setting or the remote monitoring setting. For example, an encoding protocol having redundant data is effective for transmitting data having a particular bandwidth at a long range or in the presence of an interfering signal. In one example, the encoding protocol is selected such that the transmitted signal bandwidth is much greater than the bandwidth of the information or data. In other words, by introducing a varying degree of redundancy in the encoded signal, or by selecting alternative encoding protocols, the present subject matter alters the ratio of the information bandwidth relative to the transmitted signal bandwidth.

System

In FIG. 1, system 10 includes external device 20 and implantable device 50 configured for mutual wireless communication.

External device 20 includes processor 24 coupled to memory 22, clock 26, transceiver 28 and interface 30. Interface 30 is further coupled to data input 32 and data output 34. In one example, the combination of data input 32 and interface 30 is referred to as an input interface and is configured to receive input data for controlling implantable device 50. In one example, the combination of data output 34 and interface 30 is referred to as an output interface and is configured to provide output information based on a sequence of data units received from implantable device 50.

External device 20, in various examples, include a repeater and a programmer. Processor 24, in various examples, is implemented in circuitry to perform signal processing, a microprocessor configured to execute instructions, or any combination thereof. Processor 24 is configured to implement a method as described elsewhere in this document. Memory 22 provides storage for instructions and data. Memory 22 includes, in various examples, read only memory, random access memory, removable memory and other types of memory. Clock 26 provides timing signals for implementing a method executed by external device 20.

Transceiver 28, in one example, includes a far field radio frequency transmitter and a far field radio frequency receiver. Data input 32 receives instructions or data for use by external device 20 or implantable device 50. Data input 32, in various examples, includes memory, a keyboard, a mouse, a trackball, an optical device, an audio transducer or other data input device. Data output 34 renders data derived from external device 20 or implantable device 50. Data output 34, in various examples, includes a printer, a display, a memory and an audio transducer. In one example, data input 32 and data output 34 are combined in a single device. For example, in various examples, data input 32 and data output 34 are instantiated by a touch-sensitive screen or a network interface for coupling to a communication network, such as an Ethernet or other local area network or the internet or other wide area network. Interface 30 serves as an interface between data input 32, data output 34 and processor 24. The foregoing description of external device 20 is not exhaustive and other components or more components are also contemplated. In one example, external device 20 includes multiple processors, only one of which is illustrated in the figure and described herein as processor 24. External device 20, in various examples is powered by a metered line service, a battery, or a telephone loop current.

External device 20, according to various examples of the present subject matter, includes a programmer or repeater to facilitate communications with implantable device 50.

Implantable device 50 includes processor 54 coupled to memory 52, clock 56, transceiver 58 and interface 60. Interface 60 is further coupled to therapy circuit 62 and monitor circuit 64. Implantable device 50, in various examples, includes a cardioverter, a cardio defibrillator, a pacemaker, a therapy device or a monitoring device. Processor 54, in various examples, is implemented in circuitry to perform signal processing, a microprocessor configured to execute instructions, or any combination thereof. In one example, processor 54 includes circuitry or programming to implement an error detection algorithm. Processor 54 is configured to implement a method as described elsewhere in this document. Memory 52 provides storage for instructions or data, sometimes referred to as data units. Memory 52 includes, in various examples, read only memory, random access memory and other types of memory. Clock 56 provides timing signals for implementing a method executed by implantable device 50. Transceiver 58, in one example, includes a far field radio frequency transmitter and a far field radio frequency receiver. Therapy circuit 62 delivers therapy to an organ as a function of a signal received from processor 54. Therapy circuit 62, in one example, includes a pulse generator circuit for delivering electrotherapy. Therapy circuit 62, in one example, includes a drug release circuit for delivering a chemical agent as a function of a signal received from processor 54. Monitor circuit 64, in various examples, includes sensors or other devices and circuitry to monitor physiological conditions or events. Monitor circuit 64, in one example, includes sensors and circuitry to monitor parameters and values associated with implantable device 50. In one example, monitor circuit 64 includes a transthoracic impedance measurement circuit. In one example, therapy circuit 62 and monitor circuit 64 are combined in a single device. Interface 60 serves as an interface between therapy circuit 62, monitor circuit 64 and processor 54. In one example, processor 54 is configured to receive a series of data units from a data source such as, for instance, interface 60 (or therapy circuit 62 and monitor circuit 64), clock 56, memory 52 or other data source. The foregoing description of implantable device 50 is not exhaustive and other components or more components are also contemplated. In one example, implantable device 50 includes multiple processors, only one of which is illustrated in the figure and described herein as processor 54. Implantable device 50, in various examples, is powered by a battery or other energy storage device.

Data Structures

Implantable device 50 and external device 20 are configured to communicate messages encoded as digital data. The messages, in one example, are encoded with redundant data which, for a given data rate, reduces the data throughput rate. The encoding protocol allows for a greater communication range at a given error rate or a reduced error rate for a given communication range.

Circuitry or programming of implantable device 50 and external device 20 are configured to encode and decode data according to the methods disclosed herein. In various examples, processor 54 of implantable device 50, or processor 24 of external device 20, includes instructions which, when executed, encode an outbound message based on a characteristic of the communication channel or other parameter. In addition, in one example, processor 54 of implantable device 50, or processor 24 of external device 20, includes instructions which, when executed, decodes an inbound message.

The noise in the communication channel causes symbol errors with a certain probability and determines a channel capacity expressed as the bits of information per symbol that can be sent. By selecting an encoding protocol at the transmitter and operating below the channel capacity, a desired communication range can be achieved with a sufficiently low error rate at the receiver.

In one example, the sending device encodes information into digital data and the receiving device decodes the digital data to recover information. In one example, the communication channel capacity is fixed by the transmitter. In particular, the communication channel capacity is limited by various factors, including the battery, the antenna, the transmitter and other structures of the implantable device as well as controlling regulatory bodies (such as the Federal Communications Commission).

An example of an encoding protocol suitable for use with the present subject matter includes repetition coding. Repetition coding entails providing a duplicate unit of information with each encoded message, or codeword, sent. For example, if the unit of information includes a data sequence of 10011, then, according to one example, a transmitted frame encoded with repetition coding may appear as a codeword of {header} {10011 10011 10011 10011} {footer} where the unit of information is repeated by a factor of four. In this example, the header and footer include identification information, flags and other error checking or detection codes. According to one example, the header or footer includes an error checking code such as a parity bit, a checksum, a cyclic redundancy code or other code which facilitates data communication. A portion of the codeword includes a number of duplicated instances of the original data sequence.

Some error detection algorithms, such as cyclic redundancy code or parity code, provide a measure of redundancy. However, as used in this document, the level of redundancy refers to redundancy which allows for detecting errors and correcting errors. In addition, the level of redundancy is selectable based on the noise in the communication channel, an error rate or other criteria.

In one example, the decoding scheme for repetition coding includes correlating the received data to improve noise performance at the expense of data bandwidth. By way of example, correlating includes executing a majority voting algorithm using a sequence of bits. For a system that relies on frequent bit value changes, the blocks of code are re-transmitted multiple times and correlated at the receiving device to decode the data block by block. Correlation of received data, in one example, is implemented as a post-processing procedure performed on the received data.

In one example, a confidence level is attributed to each bit of data. A demodulator in the receiving device decodes the data to determine the symbol as well as a degree of confidence for the symbol. For example, in a frequency shifted key encoding scheme, the receiving device may be aware, with a high level of confidence, that a particular bit has a value of 1. A weighted voting scheme is applied at the receiving device to discern the transmitted bit where the weight is determined by the confidence level. The transmission efficiency is increased with a confidence level attributed to each bit of data. In one example, those bits having a having a high confidence level are efficiently passed on and those bits with a low confidence level receive the focus of attention (and thus, further processing). Other decoding schemes are also contemplated using a confidence level.

Majority voting relies on established rules whereby the unit of information is deemed to be of a particular value as determined by a majority of the duplicate strings received in the codeword. Continuing with the example above, if the received codeword included a single bit error in the last bit of the third instance of the data sequence, namely, {header} {10011 10011 10010 10011} {footer}, then by majority voting, the receiver would properly decode the last bit as a 1 since three votes indicate a 1 and a single vote indicates a 0.

Another example of an encoding protocol suitable for use with the present subject matter includes a pseudo random sequence code. In this example, a pseudo random sequence string is ascribed a digital value of 1 and the inverse of the pseudo random sequence string is ascribed a digital value of 0. By way of example, if the unit of information is 1010 and a randomly selected sequence (sometimes called a chip) is 10011, then a portion of the corresponding codeword is expressed as 10011 01100 10011 01100. As indicated above, a header and footer may be provided as well. In one example, the length of the chip is increased to provide an increased level of redundancy and reduced to provide a lower level of redundancy.

In one example, a form of error correction called forward error correction (FEC) is applied to the telemetry link. Forward error correction is effective when the transmitter cannot readily verify if data was received correctly such as with, for example, a simplex communication link.

Forward error correction techniques employ redundant data which reduces the information rate as well as the error rate. With forward error correction, additional information and redundancy is provided to the receiver which assists in recovery of the data stream. The burden of detecting and correcting errors falls on the receiving device.

Three representative types of forward error correction include block codes, convolutional codes and interleaving.

Block codes operate on bits arranged in a block. A transmitting device transmits the block as well as a coded portion added to the block by an algorithm. The data is decoded by the receiver which makes a determination as to the validity of the received sequence. Block coding is sometimes called memory-less coding.

Convolutional codes are sometimes referred to as continuous codes since they operate on a certain number of bits continuously and execute an algorithm based on a particular number of earlier bits. Adding convolutional coding, in one example, entails multiplying the signal with a pseudorandom sequence running faster than the data.

Interleaving can correct errors in fading type of channels and is sometimes used in conjunction with other types of coding. Interleaving spreads errors across multiple packets. Examples include frequency interleaving and time interleaving.

Other types of forward error correction (for example, Reed-Solomon codes, Viterbi decoding, Hard Decision Decoding, Soft Decision Decoding, Channel State Information, Turbo coding, algebraic coding and concatenated encoding) are also contemplated and more than one encoding scheme can be combined in a parallel or serial manner.

In various examples, other encoding and decoding schemes are employed. For instance, a spread spectrum encoding and decoding scheme is implemented in one example.

The data throughput rate (and therefore the communication range) is adjusted automatically without changing the output power at the transmitter antenna and without changing the bandwidth of the transmitted data. In one example, the transmitted bandwidth of the implantable device and the transmitted bandwidth of the external device remains substantially unchanged and the data throughput rate is adjusted based on a channel characteristic. In another example, the transmitted bandwidth of the external device varies according to a channel characteristic while the transmitted bandwidth of the implantable device remains substantially unchanged.

In one example, the sending device encodes the message using one of a plurality of encoding protocols which allows the receiving device to detect and correct an error without requesting retransmission of the original information.

By way of example, assume the packet size is 128 bytes in length and the raw instantaneous bit error rate is $10^{-5}$. Accordingly, in an automatic request-repeat system, in which the sender requests a retransmission (for example, in the event of an error) the effective data rate is 99% of the link data rate. In other words, the rate at which raw bits are being transmitted is 99% of the channel capacity since 1% of the link rate is lost in re-transmits of previously corrupted packets.

If, however, the range is increased and the instantaneous bit error rate rises to approximately $10^{-2}$, then, in an automatic request-repeat system, the effective data rate drops to less than 3.4% of the link data rate. In contrast, if a repetition code is used in which each data bit is sent five times, and a majority voting algorithm is implemented to determine the proper bit, then the signal at the output antenna can be reduced by 5 dBm and still achieve the bit error rate of $10^{-5}$. According to one example, a reduction of 5 dBm allows for a doubling of the link distance between the sending device and the receiving device.

In one example, the transmitted signal bandwidth is much greater than the information bandwidth and the ratio of the information bandwidth is altered relative to the transmitted signal bandwidth. The ratio is altered by introducing a varying degree of redundancy or by executing alternative encoding protocols. In addition, the transmitted signal bandwidth remains substantially constant.

Method

In one example, the external device (such as, for example, a repeater or a programmer) and the implantable device are in a master-slave relationship. The master, or external device, initiates a request for data from the slave, or implantable device. The implantable device is configured to monitor for a communication session request at particular times. In one example, the implantable device periodically wakes up and monitors for a session request, and if detected, then the implantable device transitions to another mode in which later data is received.

Figure 2:
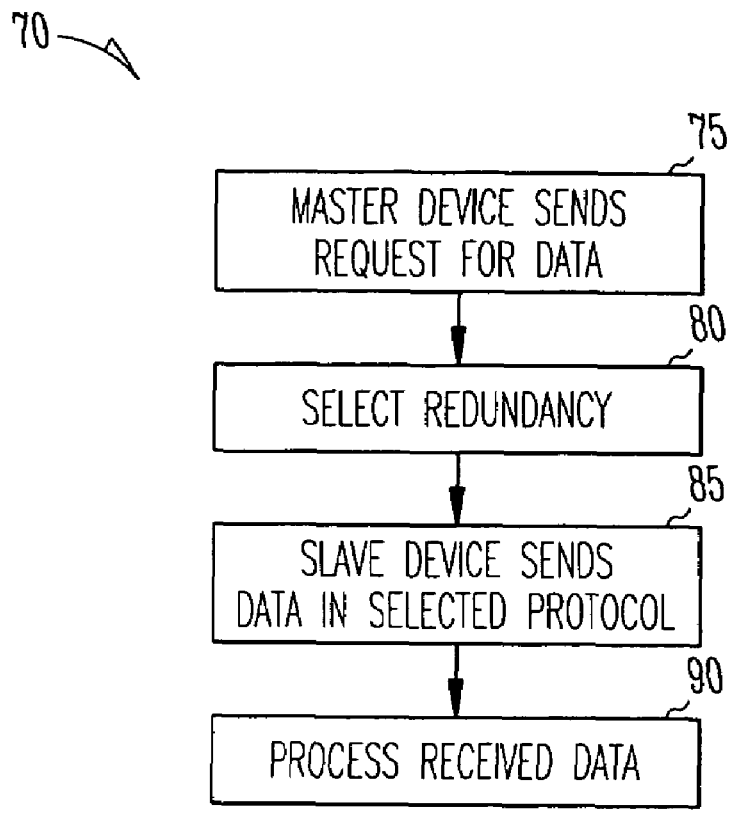
FIG. 2 illustrates a flow chart of a method according to one example.

FIG. 2 illustrates a flow chart of method 70 according one example in which the external device serves as a master device and the implantable device serves as the slave device. At 75, the master device generates and sends a request for data to the slave device. In various examples, the request is sent in a protocol selected from a plurality of protocols or the request is sent without redundancy. Upon receiving the request, the slave device, at 80, selects a protocol for the reply based on a channel characteristic discernable from the request or based on an identification code specified as part of the encoded request. In one example, at 80, the master device selects a protocol for the reply based on a channel characteristic discerned from a previous communication with the slave device or based on another parameter. At 85, the slave device transmits the reply using the selected protocol. As noted, the protocol may have been selected by the master device or by the slave device. The master device then receives the reply and, at 90, processes the reply to decode the message.

Figure 3:
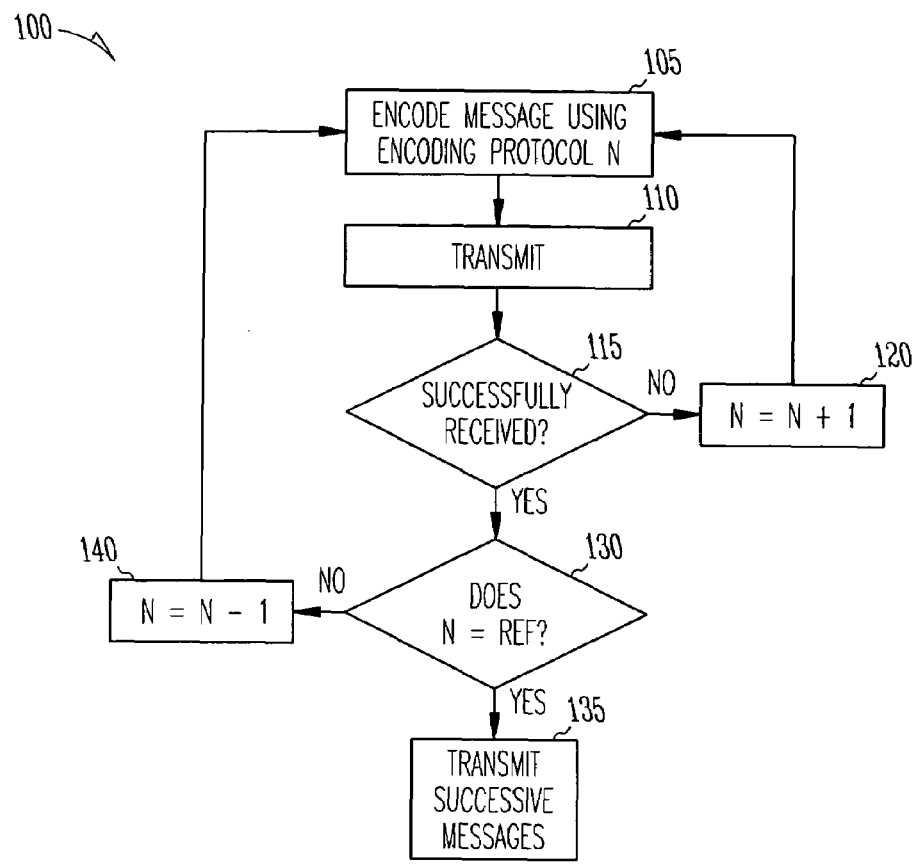
FIG. 3 illustrates a flow chart of a method according to one example.

FIG. 3 illustrates a flow chart of method 100 pursuant to one example in which a redundancy level is systematically reduced until an error rate exceeds a particular level. Both the data throughput rate and the error rate are increased with a reduction in the level of redundancy. When a particular error rate (and corresponding range) is achieved, the redundancy level is stabilized and further data exchanges occur at the stabilized level.

At 105, the sending device encodes a message, or unit of data, using encoding protocol N in which N corresponds to a particular redundancy level. This, for example, may include calculating and appending a cyclic redundancy code. At 110, the codeword is transmitted using the communication channel. In one example, the channel includes a far field radio frequency communication link, however, other links are also contemplated. At 115, the receiving device queries to determine if the message was successfully received. Successful receipt, in various examples, is established by having an error rate below a particular value at a particular communication range. If the message was not successfully received, then method 100 proceeds to 120 where the level of redundancy is increased and the message is again encoded at 105 followed by transmitting the message again at 110. If, on the other hand, the message was successfully received, then another query is executed at 130 to determine if the redundancy level is at a lowest level. In the example illustrated, this includes determining if the encoding protocol (or level of redundancy) matches a reference level. If the query at 130 is answered in the negative, then, at 140, the redundancy level is reduced, the next message is again encoded at 105 followed by transmitting the message at 110. If the query at 130 is answered in the affirmative, then at 135, later messages are transmitted at the current level of redundancy.

The iterative process described herein is exemplary and other embodiments are also contemplated. In one example, the level of redundancy is incrementally increased until a particular error rate is achieved or until a particular communication range is achieved. In one example, rather than changing the level of redundancy, the sending device encodes the digital data using one or more encoding protocols selected from among a plurality of encoding protocols, each of which offers a different combination of data throughput rate, error rate and communication range.

In one example, if the receiving device does not acknowledge receipt of a message encoded with a first encoding protocol, then the sending device transmits the same message (or a different message) using a second encoding protocol. The second encoding protocol is selected to provide a reduced error rate, thereby providing an increased communication range. The second encoding protocol, in one example, provides an increased level of redundancy.

Consider an example in which a first message is sent by a first device and, in reply, the second device then sends a second message. In one example, the first message and the second message are both encoded using the same protocol. For instance, both the first message and the second message are encoded with a repetition code wherein the message is repeated four times in each frame. In one example, the first message and the second message are encoded using different protocols. For instance, the first message is encoded using a repetition code wherein the message is repeated four times in each frame and the second message is encoded using a repetition code wherein the message is repeated eight times in each frame. In one example, the first device encodes transmitted messages using a first encoding protocol and the second device encodes transmitted messages using a second protocol that is selected based on an encoding flag received from the first device or based on other criteria.

The criteria for selecting the encoding protocol or level of redundancy may relate to the signal quality as determined by the receiver. An encoding flag, provided by the first device, is decoded by the second device and used to determine the encoding protocol used for the second message. In one example, the second device implements an encoding protocol selected as a function of time. For instance, one example provides that a particular encoding protocol is selected during specified hours of the day or at the outset of a communication session and a second encoding protocol is selected at other times or for later exchanges during a communication session. The encoding flag, in various examples, is included with, or appended to, the codeword. In one example, the first message is devoid of redundancy and the second message includes a particular level of redundancy.

In one example, either the sending device or the receiving device determines a value for a characteristic of the communication channel and uses the value in selecting an encoding protocol for a later message. For instance, if the noise on the communication channel exceeds a particular value, then later frames are sent using an encoding protocol selected to provide a reduced error rate. This may entail applying an encoding protocol having a greater level of redundancy.

The encoding protocol selected for later frames may have a reduced level of redundancy. For example, where the error rate of the first message is acceptably low, the second message can be encoded with a protocol that provides increased data throughput at the expense of an increase in error rate.

In one example, when the bit error rate is sufficiently low, an automatic request-repeat communication system is used. However, at an increased link distance, or in the presence of an interfering signal, the bit error rate will generally rise (namely, the signal to noise ratio drops). In this example, after the first device (or the second device) determines that the error rate has risen to an unacceptably high level using automatic request-repeat, later communications are conducted using an encoding protocol selected to provide a reduced error rate.

For instance, the first device and the second device communicate using a level of redundancy determined as a function of a characteristic of the communication channel or other parameter.

Exemplary Alternatives

The receiving device can be configured to reply to the sending device using a message with an encoding protocol, or level of redundancy, determined based on a characteristic associated with the communication channel. In addition, the receiving device can be configured to request or instruct the sending device to send a later (or current) frame using an increased level of redundancy.

In one example, the encoding protocol (for instance, a level of redundancy in the transmitted data) is determined as a function of the signal strength of the received signal. For example, a low signal strength invokes a reply having a high level of redundancy and a high signal strength invokes a reply having a lower level of redundancy. Accordingly, one example of a receiving device includes programming or circuitry to evaluate signal strength and compare the signal strength with a reference value. As a function of the comparison, the receiving device provides a signal to the sending device to request a change in the encoding protocol.

In one example, the encoding protocol is selected to provide a high level of redundancy at the outset of the communication session and later frames of data are sent at a reduced level of redundancy provided that the earlier frames are received with an acceptably low error rate.

In various examples, the encoding protocol includes sufficient redundancy to allow the receiving device to correct an error or allow the receiving device to request a retransmission of a frame.

In one example, the encoding protocol (for instance, the level of redundancy) is changed dynamically. The power consumption of the implantable device may vary according to the encoding protocol selected. As such, one example provides that a first encoding protocol associated with a lower power consumption is used for some transmissions and a second encoding protocol associated with a higher power consumption is used for other transmissions. The implantable device selects the encoding protocol based on an instruction or flag received from the external device or based on a measured criteria or other parameter.

In one example, the encoding protocol is selected as a function of the external device. For instance, if the external device is a repeater, then the implantable device utilizes a first encoding protocol and if the external device is a programmer, then the implantable device utilizes a second encoding protocol. In particular, if the external device is a repeater, then a longer range and a lower throughput rate is acceptable whereas for a programmer, the range is generally shorter and the throughput is higher. The implantable device selects a particular encoding protocol as a function of a code received in a frame transmitted by the external device.

In one example of an implantable device, the data bandwidth is substantially fixed and the data throughput rate is adjusted based on an encoding protocol (such as level of redundancy).

In one example, the implantable device implements an encoding protocol having a low throughput of data, thus communicating data over a relatively long range. Such a configuration may be suitable for use with a repeater used in a patient's home. The repeater is configured for connecting with a communication network such as a local area network (for example, an Ethernet) or a wide area network (such as the Internet). In one example, the connection includes a telephone interface for connecting with a POTS network. As such, the level of redundancy effectively enhances the signal to noise ratio by reducing the noise floor.

In one example, both the implantable device and the external device are configured to transmit data encoded with a selectable encoding protocol, such as a variable level of redundancy. In one example, either the implantable device or the external device is configured to encode transmitted data with a variable level of redundancy.

In one example, the session request transmitted by the external device is encoded with a first encoding protocol and a later message in the same session is encoded with a second, and different, encoding protocol. In one example, the first encoding protocol includes a greater amount of redundant data than the second encoding protocol. In one example, the first encoding protocol includes the greatest level of redundancy and after the communication session has been initiated, the level of redundancy is incrementally reduced, until a particular error rate is met or until a particular data throughput rate is achieved. As the level of redundancy is reduced, the error rate is expected to increase and when a particular error rate is observed, then, in one example, the level of redundancy is again slightly increased to provide an acceptable margin.

In one example, if a signal confirming successful receipt of a message is absent, then the transmitting device will send a later frame using an encoding protocol or an increased level of redundancy having a range greater than the protocol used with the initial message.

In one example, if the communication channel remains silent for a sufficiently long time period after having most recently transmitted a frame using a first encoding protocol, then the next message is transmitted using a second, and different, encoding protocol. In one example, the second encoding protocol has a level of redundancy greater than that of the first encoding protocol. In one example, the level of redundancy is incrementally increased until an acceptable error rate is achieved. In one example, the encoder is configured to encode a first frame at the maximum level of redundancy following the silent period and to encode a later frame at a reduced level of redundancy.

In one example, the receiving device is tasked with executing an algorithm to discern the encoding protocol of the message or determine the level of redundancy. In one example, a flag in a packet header denotes that the packet is encoded with redundant data. For example, the flag may indicate that the flag alone is the only redundant element or the flag may indicate that the entire packet includes redundant data.

Because of the limited power supply availability and physical size constraints, the processing capacity of an implantable device is typically comparatively less than that of an external device. As such, in one example, the external device is configured to transmit a message with a particular level of redundancy and the implantable device is configured to transmit data without redundancy.

In various examples, either one or both of the implantable device and the external device are configured to encode and transmit redundant data.

In one example, the level of redundancy is increased with each retransmission of a particular message until an acceptable range or error rate is achieved.

In one example, an acknowledgement message is sent in reply to a request message from a sending device and the acknowledgement message is transmitted at a redundancy rate determined as a function of the request message. For example, if the request message is encoded with a first level of redundancy, then the acknowledgment message is also encoded with the first level of redundancy.

In one example, the first encoding protocol and the second encoding protocol differ in terms of the length of a data packet, or packet size. For instance, the reply can be encoded with data packets having a longer or shorter length. In one example, the packet size is adjusted based on channel characteristics. In other words, a variable amount of data is included in each frame and since the frame overhead (header, footer, error detection) remains unchanged, a larger frame is more efficient. For example, a first transmitted message, including a large amount of data, is transmitted in a first frame and if the channel characteristics indicate that the message was not received with a sufficiently low error rate, then a second frame is encoded using a portion of the large frame and the second frame is transmitted. Again, the error rate is evaluated and if warranted, another reduction in the frame size is made and another transmission is sent. As such, the size of the frame is successively reduced until an acceptable error rate is achieved. In one example, the size of any successive frame is half that of the prior frame. In addition, successive frames can be sent having a length that is increased until a target error rate is achieved.

The present subject matter is described relative to wireless communications using far field radio frequency transmission and reception. However, the disclosed subject matter is also suitable for use with near field transmission and reception, such as that provided by inductive coupling, magnetic coupling or other communication means.

In one example, the encoding protocol, or the level of redundancy, is selected as a function of an error rate calculated based on a previously received reply signal. In various example, the encoding protocol or level of redundancy is determined based on other criteria. According to one example, when communicating in an environment known to be noisy, the programmer is configured to select a particular encoding protocol or redundancy level.

Other methods of operating an implantable device are also contemplated. The various methods provide, in different examples, a selectable communication range, a selectable power consumption level, a selectable data communication rate and a selectable output transmit power level.

For example, a data rate can be selected to yield a desired communication range while reducing power consumption. In addition, a raw bit rate (at the physical layer) can be selected to provide a communication rate tailored to the current use. For example, during device implantation and during an in-office visit, a higher data rate (throughput) may be desirable whereas a lower data rate at an increased communication range may be desirable while remote monitoring.

In general, the power consumed by a transmitter is not a function of the data rate. At a higher data rate, however, the time spent actually transmitting bits is reduced and therefore, the power consumed is reduced since the transmitter is powered down when not transmitting data. Thus, a higher data rate allows the transmitter to be powered on for a shorter period of time during each duty cycle.

The communication range, and the energy consumed from the battery of the implantable device, are increased both by reducing the data rate and by increasing the output power. Reducing the communication data rate increases the battery drain since more time is spent transmitting a given amount of data. Accordingly, the transmit/receive circuitry is powered up for longer time in order to transmit a given amount of data. An increased output power also increases battery drain since more current is consumed by the power amplifier when output power is increased.

In one example, the output power of the transmitter is adjusted by changing the setting of the output power amplifier. Adjusting the duty cycling corresponds to changing a communication data rate.

In one example, the average output power of the transmitter (included in transceiver 58) is an operational parameter that can be adjusted to provide a desired communication range while providing reduced power consumption. A desired power consumption level can be achieved by, for example, selecting a current level in an output power amplifier of the transmitter or by switching in or out an amplifier stage. The maximum output power of the transmitter is typically limited by a governing regulatory body. In one example, the transmitter output power is selected and held constant over a selected period of time or for a particular communication session. In one example, the transmitter output power is determined based on other criteria such as a measured parameter. Exemplary measured parameters include battery level, health of the patient or upon detection of an event. In one example, the transmitter output power is adjusted by a control signal determined by processor 54 coupled to transceiver 58, as shown in FIG. 1. Exemplary implantable circuits for use with a selectable transmitter output power include therapy circuit 62 and monitor circuit 64.

In one example, the transmitted data rate is an operational parameter that can be adjusted to provide a desired communication range, power consumption or data rate. A reduced data rate allows an increased time for sampling of the data by the receiving device. In addition, a reduced data rate effectively lowers the noise floor at the expense of a reduced communication bandwidth. In one example, the data rate is adjusted to one of a plurality of non-zero data rates by a control signal determined by processor 54 coupled to transceiver 58, as shown in FIG. 1. Exemplary implantable circuits for use with a device having an adjustable data rate include therapy circuit 62 and monitor circuit 64.

In one example, the data rate is selected based on the type of communication session to be conducted. The type of communication session, in various examples, is determined by the telemetry circuit used for communicating with the external device. For example, an inductive session may correspond to an office visit or implantation whereas a far field radio frequency communication session may be used for remote monitoring while in a patient's home.

In one example, the data rate is selected based on a command or instruction received from an external device. The instruction can be sent by a remote device, such as an external programmer, and command that the implantable device transmit data at a particular data rate. For some applications, an initial data rate may be low and an instruction may call for an increased data rate.

In one example, the data rate is selected based on the manner of initiating the communication session. In one example, the implantable device commences a session using an inductive communication link and thereafter transitions to a higher data rate using a radio frequency telemetry circuit. In one example, the implantable device commences a session at a first data rate using a radio frequency communication link and for later exchanges in the same session, a second data rate is used where the second data rate is greater than, less than or equal to the first data rate. In one example, the type of communication session, and therefore the data rate, is determined by a code provided in a data packet. In one example, the type of communication session is determined by a previous communication session.

It is to be understood that the above description is intended to be illustrative, and not restrictive. For example, the above-described examples, or any portion thereof, may be used in combination with each other. In the appended claims, the phrase "any combination" includes a single element as well as multiple elements. Furthermore, the transitional term comprising is used in the open ended sense in that elements in addition to those enumerated may also be present. Other examples will be apparent to those of skill in the art upon reviewing this document.

What is claimed is:

1. An implantable device comprising:
    an interface to receive an outbound message to be wirelessly communicated to a remote device using a communication channel;
    a processor coupled to the interface and configured to encode the outbound message with redundant data to form an encoded outbound message, the redundant data generated as a function of the outbound message and having a redundancy level selected from a plurality of redundancy levels according to a characteristic of the communication channel, wherein the redundancy level determines a number of times data is replicated within the outbound message and communicated to the remote device; and
    a far field transmitter coupled to the processor and adapted to transmit the encoded outbound message at a message throughput rate determined as a function of the redundancy level.

2. The device of claim 1 wherein the processor is adapted to encode using at least one of any combination of block coding, convolutional coding, repetition coding and pseudo random sequence coding.

3. The device of claim 1 wherein the processor includes an encoding protocol selector and the processor is configured to implement one of a plurality of encoding protocols as determined by a selector signal on the encoding protocol selector and wherein the plurality of encoding protocols includes a first encoding protocol having a first redundancy level and a second encoding protocol having a second redundancy level which differs from the first redundancy level.

4. The device of claim 1 wherein the processor includes an encoding length selector and the processor is configured to encode at one of a plurality of encoding lengths as determined by a selector signal on the encoding length selector and wherein the plurality of encoding lengths includes a first encoding length having a first redundancy level and a second encoding length having a second redundancy level which differs from the first redundancy level.

5. The device of claim 1 further including:
    an implantable receiver coupled to the processor and adapted to receive an inbound signal from the remote device;
    wherein the processor is configured to decode the inbound signal to generate an inbound message; and
    a memory coupled to the processor and adapted to store the inbound message.

6. The device of claim 5 wherein the redundancy level is selected as a function of the inbound message.

7. The device of claim 6 wherein the redundancy level is selected as a function of at least one of a signal strength of the inbound message and an error rate associated with the inbound message.

8. The device of claim 5 wherein the implantable receiver includes a far field radio frequency receiver.

9. The device of claim 5 wherein the processor includes an error detector configured to identify an error in the inbound message.

10. The device of claim 9 wherein the redundancy level is determined as a function of an error rate identified by the error detector.

11. An implantable device comprising:
a far field receiver to receive an inbound signal from a remote device via a communication channel, the inbound signal encoded with an inbound message having a variable level of redundant data, wherein the level of redundant data determines a number of times data is replicated within the inbound message, and wherein a rate of throughput of the inbound message is determined as a function of the level;
a processor coupled to the receiver and configured to determine the level from a plurality of levels according to a characteristic of the communication channel and decode the inbound message; and
a memory coupled to the processor to store the inbound message.

12. The device of claim 11 wherein the processor is configured to identify an encoding protocol used to encode the inbound signal and to decode the inbound message using at least one of a plurality of decoding protocols.

13. The device of claim 11 further including:
a data source coupled to the processor and configured to provide an outbound message; and
an implantable transmitter coupled to the processor and configured to transmit an outbound signal generated as a function of the outbound message.

14. The device of claim 13 wherein the implantable transmitter includes a far field radio frequency transmitter.

15. The device of claim 13 wherein the data source includes at least one of any combination of a monitor circuit and a pulse generator.

16. The device of claim 13 wherein the data source includes an error detector coupled to the processor and adapted to identify an error in the inbound message.

17. A method comprising:
receiving an outbound message having a first data throughput rate from an interface of an implantable device;
selecting a redundancy level from a plurality of redundancy levels for the outbound message according to a characteristic of a communication channel, wherein the redundancy level determines a number of times data is replicated within the outbound message and communicated to a remote device;
supplementing the outbound message with redundant data to form a transformed message having a second data throughput rate less than the first data throughput rate, the redundant data generated as a function of the outbound message and the selected redundancy level; and
transmitting a far field signal from the implantable device to the remote device using the communication channel, the far field signal generated as a function of the transformed message and having a message throughput rate determined as a function of the selected redundancy level.

18. The method of claim 17 wherein receiving the outbound message includes receiving an intracardiac signal.

19. The method of claim 17 wherein supplementing the outbound message with redundant data includes implementing at least one of any combination of block coding, convolutional coding, repetition coding and pseudo random sequence coding.

20. The method of claim 17 further including receiving an encoding protocol selector signal and wherein supplementing the outbound message with redundant data includes encoding the outbound message with an encoding protocol selected as a function of the encoding protocol selector signal.

21. The method of claim 17 further including:
receiving an incoming signal from the remote device;
decoding the incoming signal to generate an incoming message; and
storing data as a function of the incoming message in a memory of the implantable device.

22. The method of claim 21 wherein the incoming message includes data corresponding to an error rate and wherein supplementing the outbound message with redundant data includes implementing an encoding protocol selected from a plurality of encoding protocols based on the error rate.

23. A method comprising:
receiving, via a communication channel, an inbound signal from a remote device using a far field receiver of an implantable device, the inbound signal encoded with a level of redundant data selected from a plurality of levels according to a characteristic of the communication channel and having a message throughput rate inversely related to the selected level of redundancy, wherein the level of redundant data determines a number of times data is replicated within the inbound signal communicated from the remote device;
transforming the inbound signal by removing the redundant data to form an inbound message; and
storing the inbound message in a memory of the implantable device.

24. The method of claim 23 wherein transforming the inbound signal includes decoding the inbound signal using at least one of a plurality of decoding protocols.

25. The method of claim 23 wherein transforming the inbound signal includes decoding the inbound signal using executable instructions corresponding to at least one of any combination of block coding, convolutional coding, repetition coding and pseudo random sequence coding.

26. The method of claim 23 further including:
generating an outbound message at the implantable device; and
transmitting an outbound signal from the implantable device, the outbound signal generated as a function of the outbound message.

27. The method of claim 26 wherein transmitting includes a transmitting using a far field radio frequency transmitter.

28. The method of claim 26 wherein generating the outbound message includes receiving data from at least one of any combination of a monitor circuit and a pulse generator.

29. The method of claim 23 wherein transforming the inbound signal includes identifying an error in the inbound message.

30. The method of claim 23 wherein transforming the inbound signal includes identifying an error in the inbound message and further including:
generating an outbound message at the implantable device, the message generated as a function of the identified error; and
transmitting an outbound signal from the implantable device, the outbound signal generated as a function of the outbound message.

31. A device comprising:
an input interface to receive an outbound message to be communicated to an implantable device using a communication channel;
a processor coupled to the interface and configured to encode at least a portion of the outbound message with redundant data to form an encoded outbound message and having a redundancy level selected from a plurality of redundancy levels according to a characteristic of the communication channel, the redundant data generated as a function of the outbound message, and wherein the redundancy level determines a number of times data is replicated within the outbound message and communicated to the implantable device; and a far field transmitter coupled to the processor and adapted to transmit the encoded outbound message at a message throughput rate inversely related to the redundancy level.

32. The device of claim 31 wherein the processor is adapted to encode using at least one of any combination of block coding, convolutional coding, repetition coding and pseudo random sequence coding.

33. The device of claim 31 wherein the processor includes an encoding protocol selector and the processor is configured to implement one of a plurality of encoding protocols as determined by a selector signal on the encoding protocol selector and wherein the plurality of encoding protocols includes a first encoding protocol having a first redundancy level and a second encoding protocol having a second redundancy level which differs from the first redundancy level.

34. The device of claim 31 wherein the processor includes an encoding length selector and the processor is configured to encode at a redundancy length as determined by a selector signal on the encoding length selector and wherein the plurality of encoding lengths includes a first encoding length having a first redundancy level and a second encoding length having a second redundancy level which differs from the first redundancy level.

35. The device of claim 31 wherein the input interface includes at least one of any combination of a keyboard, a mouse, a trackball, a touch sensitive screen, a network interface and a memory.

36. The device of claim 31 further including:
a receiver coupled to the processor and adapted to receive an inbound signal from the implantable device, wherein the processor is configured to decode the inbound signal to generate an inbound message; and
an output device coupled to the processor to receive the inbound message.

37. The device of claim 36 wherein the output device includes at least one of any combination of a display, a printer, a memory and a network interface.

38. The device of claim 36 wherein the receiver includes a far field radio frequency receiver.

39. The device of claim 36 wherein the processor includes an error detector configured to identify an error in the inbound message.

40. The device of claim 39 wherein the processor is adapted to encode the outbound message using redundancy level selected as a function of an error rate determined by the error detector.

41. A device comprising:
a far field receiver to receive, via a communication channel, an inbound signal from an implantable device, the inbound signal encoded with redundant data and having a redundancy level selected from a plurality of redundancy levels according to a characteristic of the communication channel and having a message throughput rate inversely related to the redundancy level, wherein the level of redundant data determines a number of times data is replicated within the inbound signal communicated from the implantable device;
a processor coupled to the receiver and configured to decode the inbound signal to remove the redundant data and form an inbound message; and
a memory coupled to the processor to store the inbound message.

42. The device of claim 41 wherein the processor is configured to decode the inbound signal using at least one of a plurality of decoding protocols.

43. The device of claim 41 further including:
a data source coupled to the processor and configured to provide an outbound message; and
a transmitter coupled to the processor and configured to transmit an outbound signal generated as a function of the outbound message.

44. The device of claim 43 wherein the transmitter includes a far field radio frequency transmitter.

45. The device of claim 43 wherein the data source includes at least one of any combination of a keyboard, a mouse, a trackball, a touch sensitive screen, a network interface and a memory.

46. The device of claim 43 wherein the data source includes an error detector coupled to the processor and adapted to identify an error in the inbound message.

47. The device of claim 41 wherein the memory is coupled to at least one of any combination of a display, a printer, a memory and a network interface.

48. A method comprising:
receiving an outbound message from an interface of an external device;
supplementing the outbound message with redundant data to form a transformed message, the redundant data generated as a function of the outbound message and having a redundancy level selected from a plurality of redundancy levels according to a characteristic of a communication channel, wherein the redundancy level determines a number of times data is replicated within the outbound message and communicated to an implantable device; and
transmitting a far field signal from the external device to the implantable device using the communication channel, the far field signal generated as a function of the transformed message and having a message throughput rate inversely related to the redundancy level.

49. The method of claim 48 wherein receiving the outbound message includes receiving data from at least one of any combination of a keyboard, a mouse, a trackball, a touch sensitive screen, a network interface and a memory.

50. The method of claim 48 wherein supplementing the outbound message with redundant data includes implementing at least one of any combination of block coding, convolutional coding, repetition coding and pseudo random sequence coding.

51. The method of claim 48 further including receiving an encoding protocol selector signal and wherein supplementing the outbound message with redundant data includes encoding the outbound message with an encoding protocol selected as a function of the encoding protocol selector signal.

52. The method of claim 48 further including:
receiving an inbound signal from the implantable device;
decoding the inbound signal to generate an inbound message; and
storing data as a function of the inbound message in a memory of the external device.

53. The method of claim 52 wherein the inbound message includes data corresponding to an error rate and wherein supplementing the outbound message with redundant data includes implementing an encoding protocol selected from a plurality of encoding protocols based on the error rate.

54. A method comprising:

Receiving, via a communication channel, an inbound signal from an implantable device using a far field receiver of an external device, the inbound signal encoded with redundant data having a redundancy level selected from a plurality of redundancy levels according to a characteristic of the communication channel and having a message throughput rate inversely related to the redundancy level, wherein the redundancy level determines a number of times data is replicated within the inbound signal and communicated from the implantable device;

transforming the inbound signal by removing the redundant data to form an inbound message; and storing the inbound message in a memory of the external device.

55. The method of claim 54 wherein transforming the inbound signal includes decoding the inbound signal using executable instructions corresponding to at least one of any combination of block coding, convolutional coding, repetition coding and pseudo random sequence coding.

56. The method of claim 54 further including:
generating an outbound message at the external device; and
transmitting an outbound signal generated as a function of the outbound message.

57. The method of claim 56 wherein transmitting includes a transmitting using a far field radio frequency transmitter.

58. The method of claim 56 wherein generating the outbound signal includes receiving data from at least one of any combination of a keyboard, a mouse, a trackball, a touch sensitive screen, a network interface and a memory.

59. The method of claim 54 wherein transforming the inbound signal includes identifying an error in the inbound message and further including:

generating an outbound message at the external device, the message generated as a function of the identified error; and transmitting an outbound signal generated as a function of the outbound message.

60. A method of communicating with an implantable medical device via a communication channel, the method comprising:

encoding a first outbound message with a first level of redundancy based on an encoding protocol selected according to a characteristic of the communication channel, wherein a redundancy level determines a number of times data is replicated within the outbound message;

transmitting a first outbound signal based on the first outbound message to the implantable medical device;

monitoring for an acknowledge signal within a particular time period of transmitting the first outbound signal, the acknowledge signal corresponding to the outbound signal; and if an acknowledge signal is not received within the particular time period, then transmitting a second outbound signal having a second data throughput rate less than the first data throughput rate based on a second outbound message, the second outbound signal encoded with a second level of redundancy wherein the second level of redundancy is greater than the first level of redundancy.

61. The method of claim 60 further including:
if an acknowledge signal is received within the particular time period of transmitting, then transmitting a later outbound signal at the first level of redundancy, wherein the later outbound signal follows the first outbound signal.

62. The method of claim 60 further including:
if an acknowledge signal is received within the particular time period of transmitting, then transmitting a later outbound signal at a third level of redundancy, wherein the later outbound signal follows the first outbound signal and the third level of redundancy is less than the first level of redundancy.

63. A method comprising:
receiving data, via a communication channel, at an implantable circuit coupled to an implantable transmitter;

executing an algorithm on a processor coupled to the transmitter, the algorithm adapted to generate a control signal for the transmitter according to a characteristic of the communication channel; and selecting a level of data redundancy for the transmitter as a function of the control signal, wherein the level of data redundancy determines a number of times data is replicated within a message communicated by the transmitter.

64. The method of claim 63 wherein the bit rate is determined by an instruction received from an external device.

65. The method of claim 63 wherein the control signal is determined based on a code received by an implantable receiver coupled to the implantable circuit.

66. A method comprising:
receiving data, via a communication channel, at an implantable circuit coupled to an implantable transmitter;

executing an algorithm on a processor coupled to the transmitter, the algorithm adapted to generate a control signal for the transmitter, wherein the control signal is generated according to a characteristic of the communication channel;

selecting a level of data redundancy for the transmitter as a function of the control signal, wherein the level of data redundancy determines a number of times data is replicated within a message communicated by the transmitter; and selecting one of a plurality of output power levels of the transmitter based on the control signal.

67. The method of claim 66 wherein the output power level is selected based on a parameter measured by the implantable circuit.

68. The method of claim 66 wherein the control signal is determined based on a code received by an implantable receiver coupled to the implantable circuit.

69. A device comprising:
an implantable circuit;
a processor coupled to the implantable circuit; and
a first telemetry circuit coupled to the processor, the first telemetry circuit including a transmitter configured to transmit data received from the processor via a communication channel, wherein the data is transmit with a level of redundancy determined by a control signal received from the processor, wherein the control signal is generated according to a characteristic of the communication channel, and wherein the level of redundancy determines a number of times data is replicated within a message and transmitted.

70. The device of claim 69 wherein the processor is configured to select one of a plurality of non-zero data rates for the transmitter.

71. A device comprising:
an implantable circuit;
a processor coupled to the implantable circuit; and a first telemetry circuit coupled to the processor, the first telemetry circuit including a transmitter configured to transmit data received from the processor at an output power level provided by an output amplifier having a selectable current level determined by a control signal received from the processor, wherein the control signal is determined based on a code received by a receiver included in the first telemetry circuit.

72. The device of claim 71 wherein the transmitter includes an output amplifier having a selectable current level.

* * * * *